(12) United States Patent
Prat et al.

(10) Patent No.: US 11,116,440 B2
(45) Date of Patent: Sep. 14, 2021

(54) AUTOMATED THRESHOLDING FOR UNSUPERVISED NEUROFEEDBACK SESSIONS

(71) Applicant: MENSIA TECHNOLOGIES, Chantepie (FR)

(72) Inventors: Marie Prat, Le Mesnil le Roi (FR); Louis Mayaud, Paris (FR)

(73) Assignee: CYREBRO TECHNOLOGIES, Paris (FR)

( * ) Notice: Subject to any disclaimer, the term of this patent is extended or adjusted under 35 U.S.C. 154(b) by 467 days.

(21) Appl. No.: 16/063,022

(22) PCT Filed: Dec. 16, 2016

(86) PCT No.: PCT/EP2016/081583
§ 371 (c)(1),
(2) Date: Jun. 15, 2018

(87) PCT Pub. No.: WO2017/103208
PCT Pub. Date: Jun. 22, 2017

(65) Prior Publication Data
US 2018/0368719 A1 Dec. 27, 2018

(30) Foreign Application Priority Data
Dec. 18, 2015 (EP) .................................. 15201389

(51) Int. Cl.
*A61B 5/375* (2021.01)
*A61B 5/316* (2021.01)
(Continued)

(52) U.S. Cl.
CPC ............. *A61B 5/375* (2021.01); *A61B 5/316* (2021.01); *A61B 5/165* (2013.01); *G16H 20/70* (2018.01)

(58) Field of Classification Search
None
See application file for complete search history.

(56) References Cited

U.S. PATENT DOCUMENTS

| | | | | |
|---|---|---|---|---|
| 2002/0182574 A1* | 12/2002 | Freer | ...................... | G09B 23/28 434/236 |
| 2014/0336473 A1* | 11/2014 | Greco | .................... | A61B 5/742 600/301 |

(Continued)

OTHER PUBLICATIONS

Lansbergen et al., "ADHD and EEG-neurofeedback: a double-blind randomized placebo-controlled feasibility study", Journal of Neural Transmission, 2011, pp. 275-284, vol. 118, Issue 2.
(Continued)

*Primary Examiner* — Etsub D Berhanu
(74) *Attorney, Agent, or Firm* — Nixon & Vanderhye (57) ABSTRACT

Disclosed is a computer-implemented method for biofeedback training of a subject, the method including iteratively obtaining a series of biomarkers, each biomarker being representative of a bio-signal of the subject on a first time window; computing an intermediate threshold $\text{Thr}_{intermediate(t)}$ based on the series of biomarkers on a second time window, such that the intermediate threshold on the second time window could provide the subject with an expected reward ratio; computing a threshold $\text{Thr}_{(t)}$ as the weighted sum of the intermediate threshold $\text{Thr}_{intermediate(t)}$ and the threshold of the previous iteration $\text{Thr}_{(t-1)}$ and reporting in real-time a reward to the subject based on the difference between the biomarker and the computed threshold $\text{Thr}_{(t)}$, wherein at each iteration the time windows are moved forward in time. Also disclosed is a system for implementing the method.

19 Claims, 5 Drawing Sheets

(51) Int. Cl.
*G16H 20/70* (2018.01)
*A61B 5/16* (2006.01)

(56) References Cited

U.S. PATENT DOCUMENTS

| | | |
|---|---|---|
| 2015/0216439 A1 | 8/2015 | Muraskin et al. |
| 2015/0351655 A1 | 12/2015 | Coleman |
| 2016/0235324 A1* | 8/2016 | Mershin ............... A61B 5/4824 |

OTHER PUBLICATIONS

International Search Report, dated Mar. 21, 2017, from corresponding PCT application No. PCT/EP2016/081583.

* cited by examiner

| Time | alpha | Thr(t-1) | Thr(intermediate (t)) | Thr(t) |
|---|---|---|---|---|
| 0 | | | | 0.4 |
| δ | | | | 0.4 |
| 2δ | | | | 0.4 |
| 3δ | | | | 0.4 |
| 4δ | | | | 0.4 |
| 5δ | | | | 0.4 |
| 6δ | $\alpha_0$=0.800 | 0.400 | 0.24 | 0.371 |
| 7δ | 0.803 | 0.371 | 0.19 | 0.339 |
| 8δ | 0.806 | 0.339 | 0.25 | 0.323 |
| 9δ | 0.809 | 0.323 | 0.32 | 0.323 |
| 10δ | 0.813 | 0.323 | 0.36 | 0.329 |
| 11δ | 0.816 | 0.329 | 0.37 | 0.336 |
| 12δ | 0.819 | 0.336 | 0.38 | 0.343 |
| 13δ | 0.822 | 0.343 | 0.4 | 0.352 |
| 14δ | 0.825 | 0.352 | 0.3 | 0.344 |
| 15δ | 0.827 | 0.344 | 0.25 | 0.329 |
| ... | | | | |
| (N-1)δ | 1 | 0.244 | 0.26 | 0.244 |
| Nδ | 1 | 0.244 | 0.27 | 0.244 |

AUTOMATED THRESHOLDING FOR UNSUPERVISED NEUROFEEDBACK SESSIONS

FIELD OF INVENTION

The present invention pertains to the field of neurofeedback. More specifically, the invention relates to a system and a method for unsupervised adjustment of a threshold during a neurofeedback session.

BACKGROUND OF INVENTION

Neurofeedback is a biofeedback training which involves self-regulation of ongoing brain activity by sensory feedback. Neurofeedback may be used for various purposes, such as for instance for improving focus and attention.

Changes made in the desired direction are rewarded in a way that is understandable by a non-specialist, for instance with particular tones or pictures. On the contrary, negative feedback may be provided for undesirable or deviant brain activity.

In order to provide efficient neurofeedback training, i.e. to enable the subject to gain control of the brain activity and to train it in the desired direction, the threshold between a positive and negative reward must be finely tuned. Indeed, threshold adjustment stimulates the subjects and maintains engagement to the session.

Figure 1:
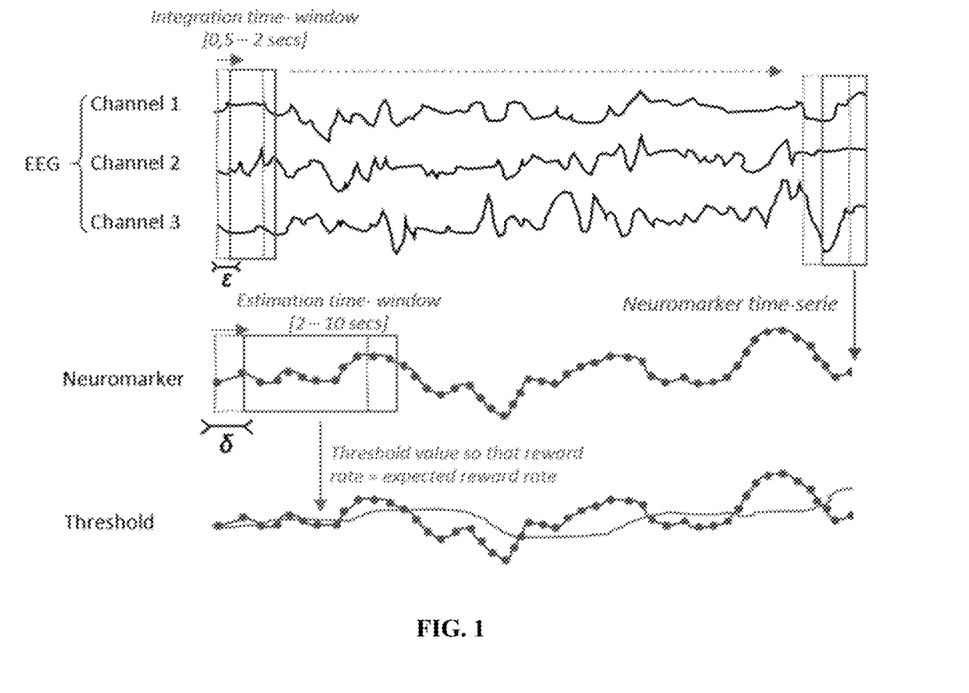
FIG. 1 illustrates the signal processing pipe from raw EEGs to the implementation of an automatic threshold with the moving average method. The neuromarker is computed from EEG signals recorded on several channels. The signal in specific frequency bands is integrated over a time window which is taken every ε seconds (also noted "the integration time window"). Said value is averaged over all electrodes, leading to a neuromarker time-series of frequency 1/ε. On said signal an "estimation time window" is taken every δ seconds and a threshold value is computed from it so that the reward ratio on the window equals to the expected reward ratio.

The actual clinical practice of neurofeedback supposes trainer supervision with manual selection of the threshold during the session. The subject's resting-state brain activity is recorded for few seconds, in order to calibrate the algorithms. Then the subject performs the training session. During sessions, his brain activity is recorded, for instance by electroencephalography (EEG) on several channels (also known as electrodes), while he performs a task. A value representative of the EEG signals (in some specific frequency ranges) is then computed. It is integrated over a time window (called "integration window"), which is taken every ε seconds (potentially overlapping time windows), and averaged over all electrodes (see FIG. 1). Said measure of activity is called hereafter a neuromarker and the consecutive integration over windows leads to a neuromarker time-series of frequency 1/ε.

The extracted neuromarker modulates a feedback that is played (auditory feedback) or displayed (visual feedback) to the subject, and that reflects the neuromarker variation. A threshold is applied on the neuromarkers so that the subject is rewarded when his activity is below or above the threshold, depending on the protocol (e.g. downtraining protocol rewards the subject if the neuromarker is below the threshold and uptraining protocol rewards the subject if the neuromarker is above the threshold). The specialist changes the threshold manually, adjusting on the subject's performance evolution and accounting for its variability. The purpose of the manual adjustment is to maintain a reward ratio that stimulates the subjects and maintain engagement: it should be neither too easy (subject is bored) nor too difficult (subject is discouraged). It is sometimes claimed that the "art" of neurofeedback resides in the practitioner's ability to adjust these thresholds values to maintain the right levels of engagement and challenge and thereby maximize efficacy.

Consequently, neurofeedback sessions have to be performed by the subject with assistance of a trained specialist. Said supervision considerably limits availability of neurofeedback sessions. Moreover, it also limits feasibility studies and repeatability.

Unsupervised automatic adjustment of the threshold has also been implemented. Existing automatic thresholding systems are implemented based on a moving average time window. A time window, that generally lengths few seconds (also named "estimation time window"), moves forward with a regular pace of δ seconds (potentially overlapping time windows). On every window, a threshold is computed (see FIG. 1) such that it provides rewards at an expected reward rate (also referred to as "expected reward ratio"). Said type of threshold has three major drawbacks: first, it is strongly influenced by artefacts in the EEG signal at all times. Second, a way-too-adaptive threshold does not allow the subject to learn and progress. With such automatic adjustments, the reward ratio is maintained at a constant rate whatever the actual neuromarker value, thereby hindering the conditioning and ultimately the self-modulation process that mediates the therapeutic or non-therapeutic effect. Finally, such thresholding does not mime specialist's habits who update the threshold only when subject's performances are too far from the expected reward ratio.

For example, Lansbergen et al. discloses reward threshold levels adjusted automatically based on the digitally filtered real-time EEG signal every 30 s so that the subject was rewarded about 80% of the time (Lansbergen et al., ADHD and EEG-neurofeedback: a double-blind randomized placebo-controlled feasibility study, Journal of neural transmission, 2010. DOI: 10.1007/s00702-010-0524-2). However, the analysis of Lansbergen study did not reveal significant differences between EEG-neurofeedback training group and placebo feedback group, wherein the feedback is not related to the brain activity but to a simulated EEG signal.

Consequently, automatic adjusted reward threshold according to the prior art does not work as effective as manually adjusted reward threshold.

There is therefore a need for a new method and system, wherein neurofeedback sessions can be performed by the subject without the supervision of a trainer with a preserved efficacy, the method and system being such that threshold adjustment imitates trainer practice.

Definitions

In the present invention, the following terms have the following meanings:

When the term "about" is used in conjunction with a numerical range, it modifies that range by extending the boundaries above and below the numerical values set forth. In general, the term "about" is used herein to modify a numerical value above and below the stated value by a variance of 10 percent, preferably of 5 percent.

"Biofeedback training" refers to a training which involves self-regulation of a biomarker by sensory feedback.

"Bio-signal" refers herein to any signal in subjects that can be continually measured and monitored. Bio-signal includes non-limitatively neural-signal, photopletismogram, arterial and venous blood oxygen saturation, arterial and venous blood pressure, heart rate, temperature, respiratory parameters including non-limitatively respiratory rate, tidal volume, rapid shallow breathing and respiratory variability. Bio-signal refers especially to any biological parameter that can be measured by an instrument that converts a physical measure (light, pressure, electricity, radio-signal . . . ) into an analogous signal (in volts) and which is then digitalised every ε, wherein ε is the sampling period, so that the biological signal is a digital univariate or multivariate time series at frequency 1/ε.

"EEG artefacts" are recorded signals that are non-cerebral in origin. They arise from different sources: external electrical interference, movement of the head, muscular contractions, blinks, etc.

"Electroencephalography" (EEG) refers to an electrophysiological monitoring method to record electrical brain activity. In non-invasive EEG, electrodes are placed along the scalp.

"Estimation time window" refers to a moving average time window used to compute the intermediate threshold and infer the reward percentage on said window.

"Growth rate (r)" refers to a predefined coefficient which defines the slope of the logistic model of the coefficient α.

"Learning coefficient (k)" refers to a predefined coefficient which defined the asymptote of the logistic model of the coefficient α.

"Neural signal" refers herein to the signal obtained by measuring neural activity. Said neural activity may be measured by: deep brain electrodes; electrocorticography (ECoG); electroencephalography (EEG); magnetoencephalography (MEG); magnetic resonance imaging (MRI): diffusion MRI, perfusion MRI, functional MRI (fMRI); near-infrared spectroscopy (NIRS); positron emission tomography (PET); or stereoelectroencephalography (SEEG).

"Biomarker" or "Neuromarker" refers to a value representative of a biological signal which is trained. Said values are integrated over a time window, which is taken every δ second (potentially overlapping time windows) leading to a biomarker time series of frequency 1/δ. When applied for neurofeedback, the neuromarker refers to a specific neural activity trained during neurofeedback sessions at specific locations on the scalp. For EEG neurofeedback, the neuromarker corresponds to energy levels, or ratio of energy levels, computed within specific frequency bands: alpha (8-12 Hz), beta (12-30 Hz), theta (4-8 Hz) and sensorimotor rhythms (12-15 Hz). For instance, the neuromarker is the power within two frequencies at a specific location, the power within two frequencies at a specific location divided by the power within another frequency band at a specific location, the power within two frequencies at a specific location divided by the power within a larger frequency band centered at the frequency of interest at the specific location, the power within two frequencies at a specific location divided by the signal power integrated across all frequencies or the first derivative of any of the above neuromarker.

"Real-time" means that the latency between the bio-signal record and the feedback display is shorter enough to be unnoticed by the subject. Said latency is generally less than a few seconds, or less than 1 second, or less than 500 ms or less than 100 ms.

"Resting-state bio-signal" refers to a bio-signal activity recorded while a subject is not performing any task, just resting.

"Reward": see threshold. The reward may be any sensory reward (e.g. specific tones or pictures).

"Reward ratio" refers to the percentage of reward received by the subject during a fixed period of time.

"Expected Reward ratio" refers to a predefined reward ratio.

"Reward ratio tolerance" refers to a tolerable percentage deviance around the expected reward ratio.

"Reward ratio tolerance time window" refers to a duration during which a deviance from the expected reward ratio is tolerated.

"Threshold" refers to a reference value to which the biomarker is compared. For instance, a down training protocol rewards the subject when the biomarker is maintained below the threshold during a predefined duration (see time-gating and time boosting). An up training protocol rewards the subject when the biomarker is maintained above the threshold during a predefined duration.

"Time boosting" refers to the larger time window during which the biomarker has to be maintained below the threshold (for a down training protocol) or above the threshold (for an up training protocol) in order to get an extra reward.

"Time gating" refers to the lowest time spend below the threshold (for a down training protocol) or above the threshold (for an up training protocol) in order to a get a reward.

DESCRIPTION

In a first aspect, this invention aims at proposing a computer-implemented method for biofeedback training of a subject. Said method comprising iteratively:
  obtaining a series of biomarkers, each biomarker being representative of a bio-signal of the subject on a first time window;
  computing an intermediate threshold $Thr_{intermediate(t)}$ based on the series of biomarkers on a second time window, such that said intermediate threshold on said second time window could provide the subject with an expected reward ratio;
  computing a threshold $Thr_{(t)}$ as the weighted sum of the intermediate threshold $Thr_{intermediate(t)}$ and the threshold of the previous iteration $Thr_{(t-1)}$; and
  reporting in real-time a reward to the subject based on the difference between the biomarker and the computed threshold $Thr_{(t)}$;
  wherein at each iteration the time windows are moved forward in time.

In one embodiment, the first time window used for obtaining a biomarker is referred to as the integration time window. According to one embodiment, the integration time window ranges from 0.1 second to 5 seconds, preferably from 0.5 second to 2 seconds. According to one embodiment, the integration time window is a moving overlapping window. According to one embodiment, the integration time window is a moving non-overlapping window. According to one embodiment, at each iteration the integration time window is moved forward in time with a pace ε, preferably a regular pace.

In one embodiment, the second time window used for computing the intermediate threshold $Thr_{intermediate(t)}$ is referred to as the estimation time window. According to one embodiment, the estimation time window ranges from few seconds to several tens of seconds, preferably from 2 seconds to 10 seconds. According to one embodiment, the estimation time window is a moving overlapping window. According to one embodiment, the estimation time window is a moving non-overlapping window. According to one embodiment, at each iteration the estimation time window is moved forward in time with a pace δ, preferably a regular pace. In one embodiment, the pace of the estimation time window δ differs from the pace of the integration time window ε.

In one embodiment, the reward reported in real-time to the subject is based on the difference between the current biomarker at time (t) and the computed threshold $Thr_{(t)}$ at time (t).

According to one embodiment, the expected reward ratio ranges from 10% to 100%.

According to one embodiment, the sum of the weighting factors is equal to 1.

According to one embodiment, the threshold is computed as follows:

$$Thr_{(t)} = \alpha * Thr_{(t-1)} + (1-\alpha) * Thr_{intermediate(t)}$$

wherein α is a constant or variable coefficient and ranges between 0 and 1. According to a preferred embodiment, the coefficient α ranges strictly between 0 and 1. According to one embodiment, α is not equal to 0 or 1.

Computing the threshold as explained above limits the possible values of $Thr_{(t)}$ between bounded values and prevents unwanted growth of the values of $Thr_{(t)}$.

If α equals to 0, the computed threshold $Thr_{(t)}$ matches the moving average automated threshold computed on the estimation time window $Thr_{(t)} = Thr_{intermediate(t)}$. If α equals to 1, the computed threshold $Thr_{(t)}$ reaches a plateau and the threshold at time t equals the threshold at time (t−1): $Thr_{(t)} = Thr_{(t-1)}$. The closer α is to 1, the more the weight of the threshold's history $Thr_{(t-1)}$ increases leading to computed threshold that takes past values into account. Also, as α increases the threshold progressively converges towards a constant value.

According to one embodiment, the coefficient α follows a logistic model, preferably a sigmoid model. According to one embodiment, the coefficient α is variable and $$\alpha_t = \alpha_{t-1} + r.\alpha_{t-1} * \left(\frac{k - \alpha_{t-1}}{k}\right);$$

wherein k is a learning coefficient and r a growth rate.

The coefficient α is used to compute a threshold that adapts from data and stabilizes as the threshold approaches its limit. As α increases all the way to 1, the weight of the threshold's history $Thr_{(t-1)}$ increases leading to computed threshold that takes past values into account. Also, as α increases the threshold progressively converges towards a constant value.

According to one embodiment, $\alpha_0$ ranges from 0 to 1. According to one embodiment, $\alpha_0$ ranges strictly between 0 and 1.

According to said embodiment, the coefficient α is bounded between the initial value of α (i.e. $\alpha_0$) and k, the learning coefficient. Furthermore, α converges towards k with a convergence speed that depends on the growth rate r.

k denotes the maximum values of the coefficient α, i.e. the model asymptote. According to one embodiment, k ranges from 0 to 1. For k equals to 1, the coefficient α converges towards 1 where the learning stops and $\alpha_t = \alpha_{t-1}$.

r defines the slope of the coefficient α. The higher is r, the faster is the convergence towards an asymptotic value of α. According to one embodiment, r ranges from 0 to 1.

Figure 3:
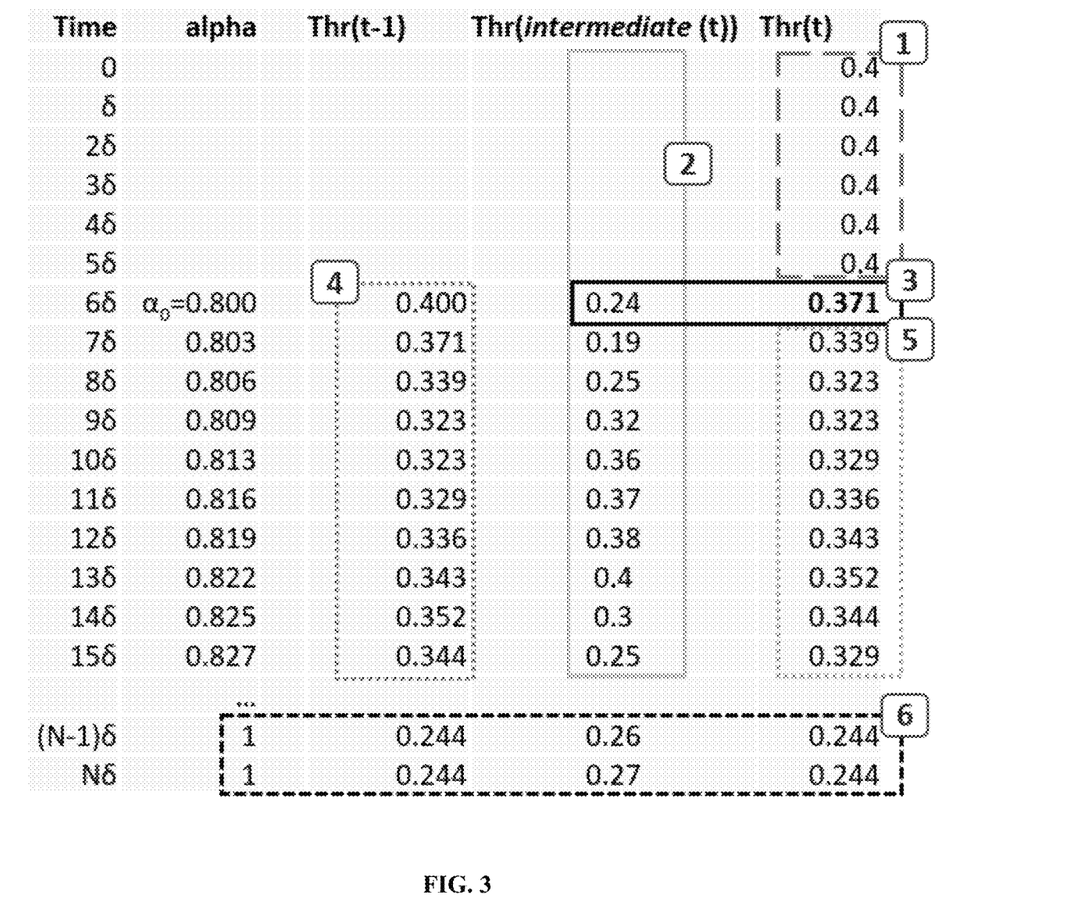
FIG. 3 illustrates the automatic threshold computation over time according to the invention.

This behaviour is illustrated in FIG. 3. The evolution of α, of the threshold computed on the previous iteration $Thr_{(t-1)}$, of the intermediate threshold $Thr_{intermediate(t)}$ and of the threshold $Thr_{(t)}$ are depicted over time. In said exemplary embodiment, $\alpha_0$ is equal to 0.8.

[1] Initial values of $Thr_{(t)}$ are computed from a previous session (calibration);
[2] $Thr_{intermediate(t)}$ is computed on an estimation time window of 5δ seconds. As long as this time has not elapsed, the threshold $Thr_{(t)}$ cannot be computed and is initialized at a predefined value. First value is computed at time 6δ;
[3] At time 6δ, a value $Thr_{intermediate(t)}$ has been computed on the estimation time window leading to an update of the $Thr_{(t)}$ value;
[4] $Thr_{(t-1)}$ equals the $Thr_{(t)}$ at time δ−1;
[5] $Thr_{(t)}$ value is computed from the previous iteration according to the formula of the present invention;
[6] When alpha reaches 1, $Thr_{(t)}$ values equals to $Thr_{(t-1)}$, and the threshold is constant and maintained over time (the boxed numbers refer to FIG. 3).

According to one embodiment, the coefficient α is reset to a predefined initial value $\alpha_0$ if the reward ratio computed during a third time window departs from more than a reward ratio tolerance around the expected reward ratio.

In one embodiment, the third time window used for resetting α is referred to as the reward ratio tolerance time window. According to one embodiment, the reward ratio tolerance time window ranges from 0 second and the session duration, preferably from 10 seconds to 1 minute.

According to one embodiment, the reward ratio tolerance ranges between 0% (no tolerance, the threshold resets every time the reward ratio computed on the estimation time window is not exactly equal to the expected reward ratio) to 100% (large tolerance, the reward ratio can take any value without inducing a threshold reset).

Figure 2:
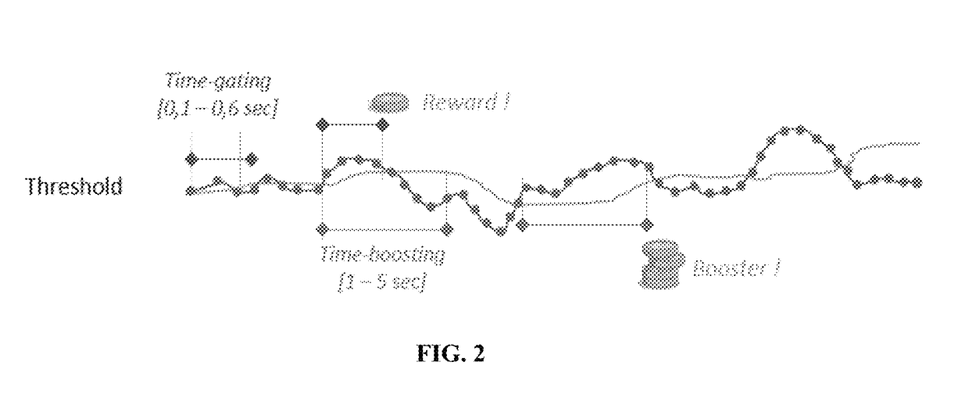
FIG. 2 illustrates the reward and booster implementation based on the neuromarker activity and the threshold level.

According to one embodiment, as depicted in FIG. 2, a first reward is reported to the subject if the subject maintained the biomarker above the computed threshold $Thr_{(t)}$ during a time longer than a time gating parameter (for an up training protocol). For a down training protocol, a first reward is reported to the subject if the subject maintained the biomarker below the computed threshold $Thr_{(t)}$ during a time longer than a time gating parameter.

So when the biomarker is trained towards a defined direction, either above or below the computed threshold $Thr_{(t)}$, a first reward is reported to the subject if the subject maintained the biomarker respectively above or below the computed threshold $Thr_{(t)}$ during a time longer than a time gating parameter. Said time gating prevents from rewarding transitory artefacts. According to one embodiment, the time gating is below 1 second, preferably ranging from 100 to 600 milliseconds.

According to one embodiment, as depicted in FIG. 2, a second reward is reported to the subject if the subject maintained the biomarker above the computed threshold $Thr_{(t)}$ during a time longer than a time boosting parameter (for an up training protocol). For a down training protocol, a second reward is reported to the subject if the subject maintained the biomarker below the computed threshold $Thr_{(t)}$ during a time longer than a time boosting parameter.

Consequently, when the biomarker is trained towards a defined direction, either above or below the computed threshold $Thr_{(t)}$, a second reward is reported to the subject if the subject maintained the biomarker respectively above or below the computed threshold $Thr_{(t)}$ during a time longer than a time boosting parameter. According to one embodiment, the time boosting is longer than the time gating. According to one embodiment, the time boosting is ranging from 1 to 5 seconds.

According to one embodiment, the initial values of the threshold are computed from a previous session or from a series of biomarkers computed from a bio-signal obtained under a given condition. Said bio-signal obtained under a given condition is for instance a resting state bio-signal.

According to one embodiment, the method according to the present invention further comprises the step of removal of artefacts from the bio-signal of the subject before computing the biomarker representative of the bio-signal on the first time window. Said removal of artefacts may be performed using any real-time artefact removal algorithms known by one skilled in the art.

According to one embodiment, the method is a computer-implemented method.

According to one embodiment, the method is a non-therapeutic method. According to said embodiment, the method may be used to improve the skills of a subject, such as for instance precision.

In a second aspect, this invention also aims at proposing a method for automated initialization of the parameters required for implementing the method for biofeedback training of a subject according to the invention, wherein the method comprises the following steps:
- obtaining a series of biomarkers of a subject from a previous session;
- obtaining a series of threshold manually chosen by an operator or trainer during said previous session; and
- identifying the optimal set of parameters that minimize an error function between the manual threshold and the threshold $Thr_{(t)}$ computed from the same series of biomarkers with the method according to the invention.

According to one embodiment, said method for automated initialization of the parameters is implemented subjectwise, on a population, or for different trainers.

According to one embodiment, the method for automated initialization of the parameters comprises:
- selecting randomly i couples of data (r, k, $\alpha_0$)$_i$ wherein i is large enough, preferably i ranges from 1 to 100 000, from 1 to 10 000 or from 1 to 1000;
- computing for each couple of data the threshold according to the present invention on the series of biomarkers;
- computing an error function between the obtained threshold and the manual threshold; and
- selecting the couple of data i with the lower error.

According to one embodiment, said method is also implemented for obtaining the following parameters: the expected reward ratio, the time gating, the time boosting, the estimation time window, the reward ratio tolerance and the reward ratio tolerance time window.

According to exemplary embodiment, the error function is a method of least squares.

According to one embodiment, said method is a computer-implemented method.

In a third aspect, this invention aims at proposing a system for implementing the method according to the first aspect of the invention. Especially, said aspect relates to a system comprising means for carrying out the method according to the first aspect.

Optionally, the invention aims to provide a computer program comprising instructions which, when the program is executed by a computer, cause the computer to carry out the method according to the first aspect of the present invention.

In another alternative, the invention aims to provide a computer-readable medium comprising instructions which, when executed by a computer, cause the computer to carry out the method of the first aspect of the present invention.

In one embodiment, said system for biofeedback training of a subject comprises:
- at least one sensor for obtaining a bio-signal of the subject;
- a computing unit for computing a series of biomarkers, each biomarker being representative of the bio-signal of the subject on a first time window; and
- a memory comprising the series of biomarkers and a set of parameters including an expected reward ratio and an initial threshold $Thr_{(0)}$;
- at least one interacting means for reporting a reward to the subject, said reward being based on the difference between the biomarker and a computed threshold $Thr_{(t)}$;

wherein the memory is connected to the computing unit for delivering the series of biomarkers and the set of parameters, and the sensor is connected to the computing unit for delivering the biomarker;

wherein the computing unit computes an intermediate threshold $Thr_{intermediate(t)}$ based on the series of biomarkers on a second time window, such that said intermediate threshold could provide the subject with an expected reward ratio;

wherein the threshold $Thr_{(t)}$ is a weighted sum of the intermediate threshold $Thr_{intermediate(t)}$ and the threshold of the previous iteration $Thr_{(t-1)}$; and wherein after each iteration the time windows are moved forward in time.

In one embodiment, the first time window used for obtaining a biomarker is referred to as the integration time window. According to one embodiment, the integration time window ranges from 0.1 second to 5 seconds, preferably from 0.5 second to 2 seconds. According to one embodiment, the integration time window is a moving overlapping window. According to one embodiment, the integration time window is a moving non-overlapping window. According to one embodiment, at each iteration the integration time window is moved forward in time with a pace ε, preferably a regular pace.

In one embodiment, the second time window used for computing the intermediate threshold $Thr_{intermediate(t)}$ is referred to as the estimation time window. According to one embodiment, the estimation time window ranges from few seconds to several tens of seconds, preferably from 2 seconds to 10 seconds. According to one embodiment, the estimation time window is a moving overlapping window. According to one embodiment, the estimation time window is a moving non-overlapping window. According to one embodiment, at each iteration the estimation time window is moved forward in time with a pace δ, preferably a regular pace. In one embodiment, the pace of the estimation time window δ differs from the pace of the integration time window ε.

According to one embodiment, the initial threshold $Thr_{(0)}$ is computed from a previous session or from a series of biomarkers computed from a bio-signal obtained under a given condition. Said bio-signal obtained under a given condition is for instance a resting state bio-signal.

In one embodiment, the reward reported in real-time to the subject is based on the difference between the current biomarker at time (t) and the computed threshold $Thr_{(t)}$ at time (t).

According to one embodiment, the expected reward ratio ranges from 10% to 100%.

According to one embodiment, the sum of the weighting factors is equal to 1.

According to one embodiment, the computing unit computes the threshold as follows:

$$Thr_{(t)} = \alpha * Thr_{(t-1)} + (1-\alpha) * Thr_{intermediate(t)}; \text{ and}$$

wherein the memory comprises a coefficient α, said coefficient being constant or variable and ranges between 0 and 1. In one embodiment, said coefficient ranges strictly between 0 and 1.

Computing the threshold as explained above limits the possible values of $Thr_{(t)}$ between bounded values and prevents unwanted growth of the values of $Thr_{(t)}$.

If α equals to 0, the computed threshold $Thr_{(t)}$ matches the moving average automated threshold computed on the estimation time window $Thr_{(t)}=Thr_{intermediate(t)}$. If a equals to 1, the computed threshold $Thr_{(t)}$ reaches a plateau and the threshold at time t equals the threshold at time (t−1): $Thr_{(t)}=Thr_{(t-1)}$. The closer α is to 1, the more the weight of the threshold's history $Thr_{(t-1)}$ increases leading to computed threshold that takes past values into account. Also, as a increases the threshold progressively converges towards a constant value.

According to one embodiment, the coefficient α follows a logistic model, preferably a sigmoid model.

According to one embodiment, the computing unit computes the coefficient α as follows:

$$\alpha_t = \alpha_{t-1} + r.\alpha_{t-1} * \left(\frac{k - \alpha_{t-1}}{k}\right);$$

and
wherein the memory comprises a learning coefficient k, a growth rate r and an initial value $\alpha_0$ of the coefficient α.

According to one embodiment, $\alpha_0$ ranges from 0 to 1. According to one embodiment, k ranges from 0 to 1. According to one embodiment, r ranges from 0 to 1.

According to one embodiment, the memory further comprises a reward ratio tolerance and a third time window; and wherein the computing unit reset the coefficient α to its initial value $\alpha_0$ if the reward ratio computed during the third time window departs from more than the reward ratio tolerance around the expected reward ratio.

In one embodiment, the third time window used for resetting α is referred to as the reward ratio tolerance time window. According to one embodiment, the reward ratio tolerance time window ranges from 0 second and the session duration, preferably from 10 seconds to 1 minute.

According to one embodiment, the reward ratio tolerance ranges between 0% (no tolerance, the threshold resets every time the reward ratio computed on the estimation time window is not exactly equal to the expected reward ratio) and 100% (large tolerance, the reward ratio can take any value without inducing a threshold reset).

According to one embodiment, the memory further comprises a time gating and a first reward is reported to the subject by the interacting means if the subject maintained the biomarker above or below the computed threshold $Thr_{(t)}$ during a time longer than a time gating parameter, depending if the biomarker is trained towards respectively above or below the threshold.

According to one embodiment, the time gating is below 1 second, preferably ranging from 100 to 600 milliseconds. According to one embodiment, the time boosting is longer than the time gating. According to one embodiment, the time boosting is ranging from 1 to 5 seconds.

According to one embodiment, the memory further comprises a time boosting and a second reward is reported to the subject by the interacting means if the subject maintained the biomarker above or below the computed threshold $Thr_{(t)}$ during a time longer than a time boosting parameter, depending if the biomarker is trained towards respectively above or below the threshold.

According to one embodiment, the computing unit further implements the step of removal of artefacts from the bio-signal of the subject before computing the biomarker representative of the bio-signal on a first time window. According to one embodiment, the computing unit further comprises a real-time artefact removal algorithms.

According to a preferred embodiment, the bio-signal is obtained using electroencephalography.

According to one embodiment, the memory further comprises a series of biomarkers of a subject and a series of thresholds manually chosen by an operator; and the computing unit identifies the optimal set of parameters that minimize an error function between the manual threshold and the threshold $Thr_{(t)}$ computed from the same series of biomarkers with the method according to the first aspect of the invention. According to one exemplary embodiment, the error function is a method of least squares.

According to one embodiment, the memory further comprises a series of biomarkers of a subject and a series of thresholds manually chosen by an operator during a previous session; and the computing unit identifies the optimal set of parameters that minimize an error function between the manual threshold and the threshold $Thr_{(t)}$ computed from the same series of biomarkers with the method according to the invention. According to one exemplary embodiment, the error function is a method of least squares.

In one embodiment, the following parameters may be automatically initialized: the expected reward ratio, the time gating, the time boosting, the second time window, the reward ratio tolerance, the third ratio tolerance time window, the growth rate, the learning coefficient and/or the initial value $\alpha_0$ of the coefficient α.

According to the Applicant, the added value of the present invention is that it has two behaviours: (i) it follows and is adjusted to the subject's biomarker—in a way similar to that of moving average models—and, (ii) it can stabilize for given periods of time, which temporarily challenges the subject. Hence, it fully allows the optimization of both the subject's engagement and his challenge.

Moreover, the way the thresholds adapts and stabilizes depends on "parameters", which can be set to cover a broad range of behaviours. For instance, the model can learn quickly and keep adjusting to subject's evolution, or it can slowly evolve and finally converge to a value. These parameters and the broad range of behaviours they generate cover the inter-operator variation of practice and make of it a versatile tool, which can be used in several ways:
  the same threshold behaviour is applied to all subjects: for instance to run a trial where the threshold selection remains consistent across all subjects;
  a subject-specific threshold behaviour (more or less challenging) is applied: for instance to challenge less subjects who seem to lack self-confidence; and
  a threshold behaviour derived (learned in the machine learning standpoint) from the manual threshold of initial sessions in order to reproduce a given specialist's habit. In said embodiment, the threshold is initialized on calibrations recorded at office or at the beginning of every training session, and its parameters are learned from specialist manual thresholding on at-office sessions.

In a fourth aspect, this invention aims at proposing a system for implementing the method according to the second aspect of the invention. Especially, said aspect relates to a system comprising means for carrying out the method according to the second aspect.

Optionally, the invention aims to provide a computer program comprising instructions which, when the program is executed by a computer, cause the computer to carry out the method according to the second aspect of the present invention.

In an alternative embodiment, the invention aims to provide a computer-readable medium comprising instructions which, when executed by a computer, cause the computer to carry out the method of the second aspect of the present invention.

EXAMPLES

The present invention is further illustrated by the following examples.

Example 1

The present invention was implemented with a set of parameters selected in order to design a threshold that complies with the following:
  initializes on a calibration session;
  adapts to data rapidly and relatively constantly;
  remains stable over time in order to challenge the subject; and
  resets when the reward percent is too far from the expected reward ratio for too long.
The chosen parameters are:
  Growth factor r=0.02 —Reward estimation time (s)=30
  Learning coefficient k=1 —Reward ratio tolerance (%)=15
  Expected reward ratio (%)=60% —Reward ratio tolerance time window (s)=30
  Time gating γ (s)=0.500 —$\alpha_0$=0.8
  Time boosting β (s)=2

Figure 4:
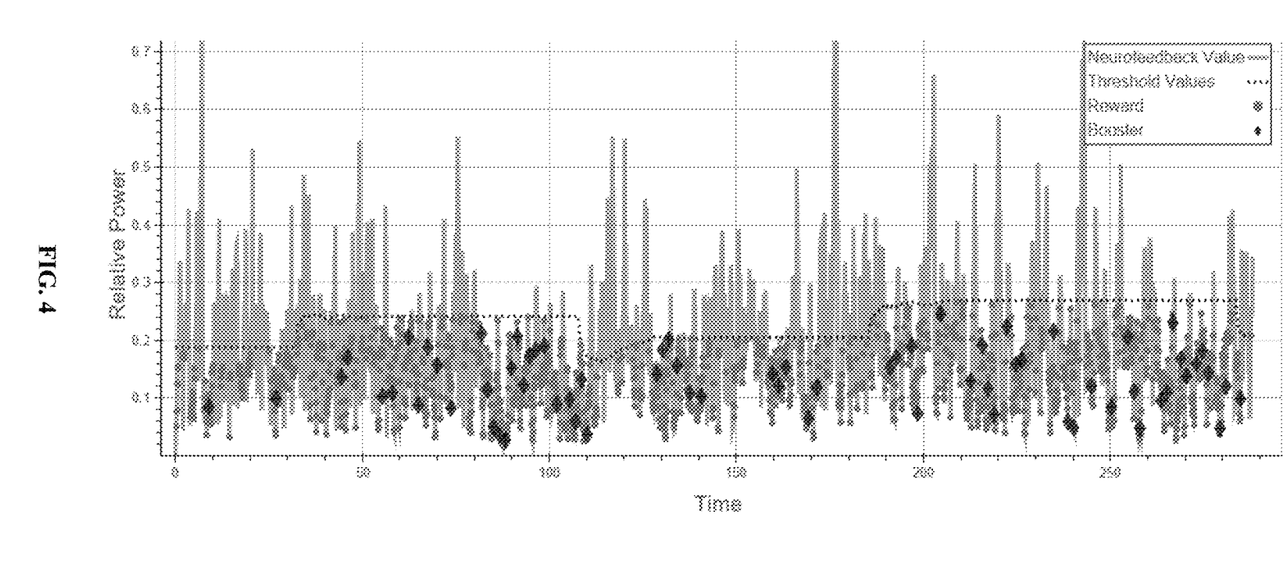
FIG. 4 illustrates the automated thresholding computed on an EEG signal according to one embodiment of the invention, see example 1. The X-axis represents the time indicated in seconds. The Y-axis represents the ratio between the signal energy in the range from 4 to 8 Hz and the signal energy in the range from 12 to 22 Hz.

The result is displayed in FIG. 4. The threshold is constant at the beginning of the signal, as it has been previously initialized on the calibration. After approximately 30 seconds in the signal, the threshold resets, and computes its new value based on the intermediate threshold's value computed on the current moving average window and previous values of the threshold, according to parameters r and $\alpha_0$, in order to provide rewards 60% of the time. The threshold is then stabilized to its new value equal to 0.25 for about 70 seconds before a new reset and a threshold value that decreases and stabilized around 0.2.

Example 2

The present invention was implemented with a different set of parameters.
  Growth factor r=0.01 —Reward estimation time (s)=30
  Learning coefficient k=1 —Reward ratio tolerance (%)=15
  Expected reward ratio (%)=60% —Reward ratio tolerance time window (s)=30
  Time gating γ (s)=0.500 —$\alpha_0$=0.3
  Time boosting β (s)=2

Figure 5A:
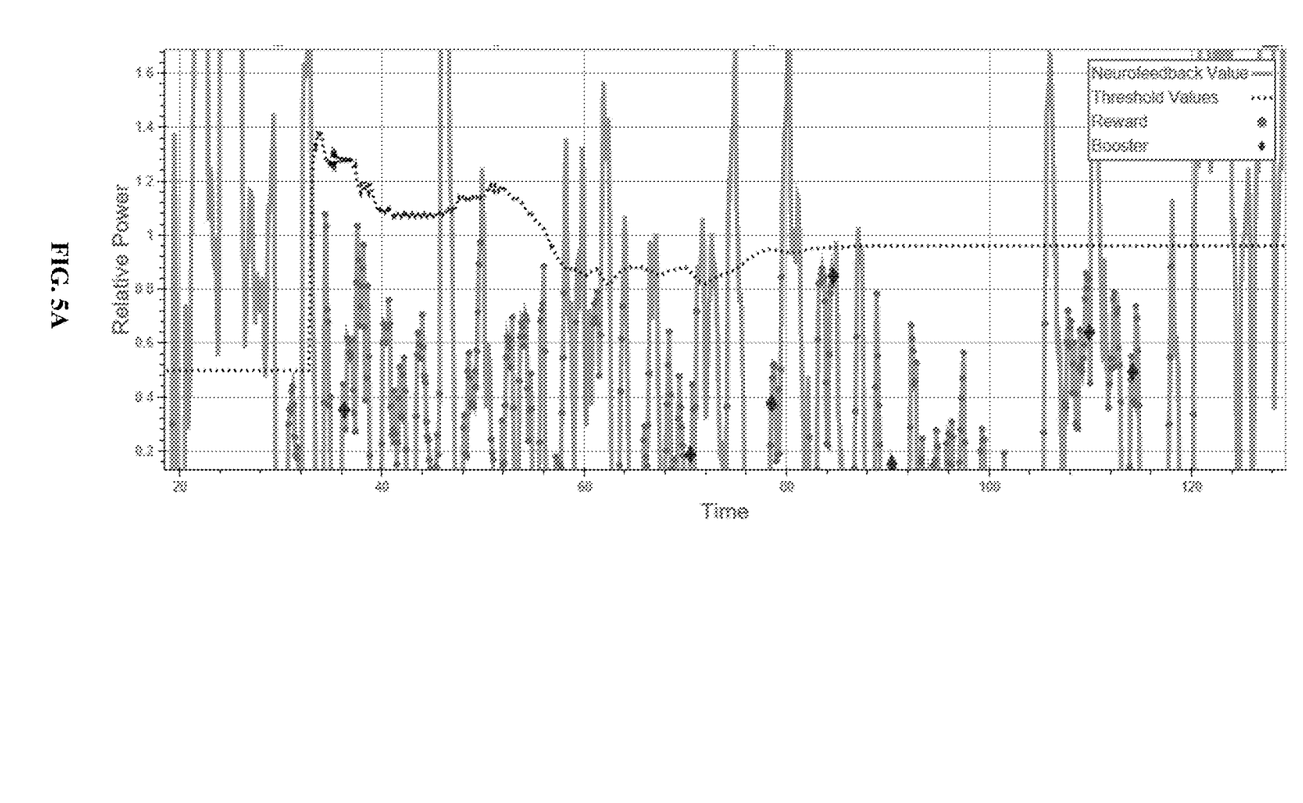
FIGS. 5A and 5B illustrates the automated thresholding computed on an EEG signal according to another embodiment of the invention, see example 2. The X-axis represents the time indicated in seconds. The Y-axis represents the ratio between the signal energy in the range from 4 to 8 Hz and the signal energy in the range from 12 to 22 Hz.
Figure 5B:
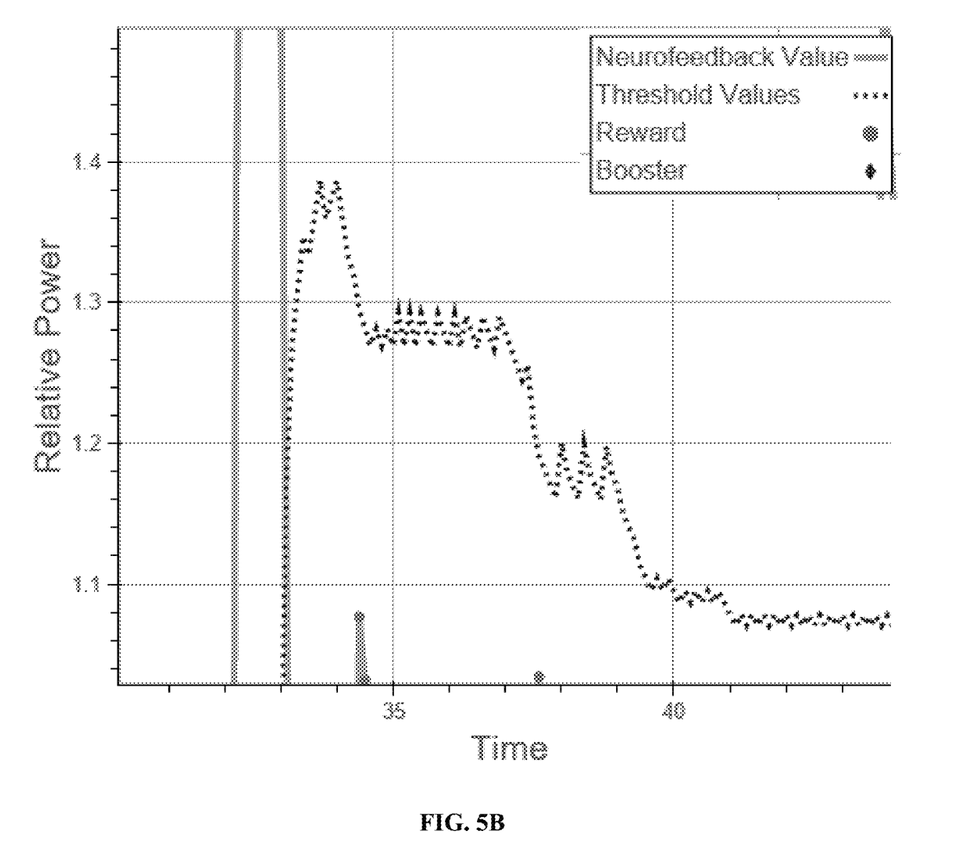

The result is displayed in FIGS. 5A and 5B. As disclosed, with lower values of r, the computed threshold is more adaptive to data but takes more time to converge toward a constant value, resulting in large oscillations before the threshold stabilization (FIG. 5A). Likewise, lower values of the initial value of α (i.e. $\alpha_0$) is associated to an unsteady threshold that oscillates a lot (FIG. 5B).

The invention claimed is:

1. A system for biofeedback training of a subject, said system comprising:
  at least one sensor for obtaining a bio-signal of the subject;
  a computing unit comprising a memory, the computing unit in communication with the at least one sensor, the computing unit configured to:
    receive the bio-signal of the subject obtained by the at least one sensor;
    for each first time window of a plurality of first time windows applied to the received bio-signal at a predefined first pace, calculate one biomarker value based on a portion of the received bio-signal in each first time window of said first time windows, so as to generate a time-series of biomarker values;
    for each second time window of a plurality of second time windows applied to the time-series of biomarker values at a predefined second pace, the second time windows corresponding to a computation time t:
      calculate an intermediate threshold $Thr_{intermediate(t)}$ based on the biomarker values comprised in said second time window, said intermediate threshold $Thr_{intermededitate(t)}$ being a reward ratio representative of a stored expected reward ratio,
      compute a threshold $Thr_{(t)}$ as a weighted sum of the intermediate threshold $Thr_{intermediate(t)}$ and a threshold of $Thr_{(t-1)}$, where $Thr_{(t-1)}$ is obtained for a previous time window corresponding to a computation time t−1, and
      calculate a difference between each biomarker value of the time-series of biomarker values and the threshold $Thr_{(t)}$;
  and at least one of a display and an auditory feedback element, for reporting a reward to the subject, where said reward is based on said difference between each value of the time-series of biomarker values and the threshold $\text{Thr}_{(t)}$.

2. The system for biofeedback training of a subject according to claim 1, wherein a sum of weighting factors of said weighted sum is equal to 1.

3. The system for biofeedback training of a subject according to claim 2,
wherein the computing unit computes the threshold $\text{Thr}_{(t)}$ as follows:

$$\text{Thr}_{(t)} = \alpha * \text{Thr}_{(t-1)} + (1-\alpha) * \text{Thr}_{intermediate(t)},$$

and wherein $\alpha$ is a coefficient that is one of constant and variable between 0 and 1.

4. The system for biofeedback training of a subject according to claim 3, wherein the coefficient $\alpha$ is computed according to a logistic model.

5. The system for biofeedback training of a subject according to claim 4,
wherein the computing unit computes the coefficient a corresponding to a computation time t as:

$$\alpha_t = \alpha_{t-1} + r.\alpha_{t-1} * \left(\frac{k - \alpha_{t-1}}{k}\right);$$

and
wherein the memory has stored therein a learning coefficient k, a growth rate r and an initial value $\alpha_0$ of the coefficient $\alpha$.

6. The system according to claim 5,
wherein the memory also stores a reward ratio tolerance and a third time window, and
wherein the computing unit resets the coefficient $\alpha$ to the initial value $\alpha_0$ if a reward ratio computed during the third time window deviates from the stored expected reward ratio by more than the reward ratio tolerance.

7. The system for biofeedback training of a subject according to claim 1,
wherein the memory has stored therein a time gating parameter, and
wherein a first reward is reported to the subject by the at least one of a display and an auditory feedback element whenever the subject maintains the biomarker values above the computed threshold $\text{Thr}_{(t)}$ for a time longer than the time gating parameter for an up training protocol, or whenever the subject maintains the biomarker values below the computed threshold $\text{Thr}_{(t)}$ for a time longer than the time gating parameter for a down training protocol.

8. The system for biofeedback training of a subject according to claim 7, wherein the memory further stores comprises a time boosting parameter and a second reward is reported to the subject by the at least one of a display and an auditory feedback element whenever the subject maintains the biomarker values above the computed threshold $\text{Thr}_{(t)}$ during a time longer than the time boosting parameter for an up training protocol, or whenever the subject maintains the biomarker values below the computed threshold $\text{Thr}_{(t)}$ for a time longer than said time boosting parameter for a down training protocol.

9. The system for biofeedback training of a subject according to claim 1, wherein the computing unit is further configured to remove artefacts from the bio-signal of the subject before computing the time-series of biomarker values.

10. A method for biofeedback training of a subject, said method comprising:
receiving a bio-signal of the subject obtained by at least one sensor;
for each first time window of a plurality of first time windows applied to the received bio- signal at a predefined first pace, calculating one biomarker value based on a portion of bio-signal comprised in said first time window, so as to generate a time-series of biomarker values;
for each second time window of a plurality of successive second time windows, each second time window of said second time windows corresponding to a computation time t:
computing an intermediate threshold $\text{Thr}_{intermediate(t)}$ based on the series of biomarker values comprised in said second time window, said intermediate threshold $\text{Thr}_{intermediate(t)}$ being a reward ratio representative of a stored expected reward ratio,
computing a threshold $\text{Thr}_{(t)}$ as a weighted sum of the intermediate threshold $\text{Thr}_{intermediate(t)}$ and a threshold $\text{Thr}_{(t-1)}$ obtained for a previous time window corresponding to a computation time t-1, and
calculating a difference between each biomarker value of said time-series of biomarker values and the computed threshold $\text{Thr}_{(t)}$; and
reporting a reward to the subject via at least one of a display and an auditory feedback element, where said reward is based on said difference between each value of the time-series of biomarker values and the threshold $\text{Thr}_{(t)}$.

11. The method for biofeedback training of a subject according to claim 10, wherein a sum of weighting factors of said weighted sum is equal to 1.

12. The method for biofeedback training of a subject according to claim 11,
wherein the threshold $\text{Thr}_{(t)}$ is computed as follows:

$$\text{Thr}_{(t)} = \alpha * \text{Thr}_{(t-1)} + (1-\alpha) * \text{Thr}_{intermediate(t)},$$

wherein a is a coefficient that is one of constant and variable between 0 and 1.

13. The method for biofeedback training of a subject according to claim 12, wherein the coefficient a follows is computed according to a logistic model.

14. The method for biofeedback training of a subject according to claim 13,
wherein $\alpha$ corresponding to a computation time t is computed as $$\alpha_t = \alpha_{t-1} + r.\alpha_{t-1} * \left(\frac{k - \alpha_{t-1}}{k}\right),$$

and
wherein k is a learning coefficient, and r is a growth rate.

15. The method for biofeedback training of a subject according to claim 12, wherein the coefficient a is reset to a predefined initial value $a_0$ if a reward ratio computed during a third time window departs from the stored expected reward ratio by more than a stored reward ratio tolerance.

16. The method for biofeedback training of a subject according to claim 10, wherein a first reward is reported to the subject by the at least one of a display and an auditory feedback element whenever the subject maintains the biomarker values above the computed threshold $\text{Thr}_{(t)}$ for a time longer than a time gating parameter for an up training protocol, or whenever the subject maintains the biomarker values below the computed threshold $Thr_{(t)}$ for a time longer than the time gating parameter for a down training protocol.

17. The method for biofeedback training of a subject according to claim 16, wherein a second reward is reported to the subject by the at least one of a display and an auditory feedback element whenever the subject maintains the biomarker values above the computed threshold $Thr_{(t)}$ during a time longer than a time boosting parameter for an up training protocol, or whenever the subject maintains the biomarker values below the computed threshold $Thr_{(t)}$ for a time longer than said time boosting parameter for a down training protocol.

18. The method for biofeedback training of a subject according to claim 10, wherein initial values of $Thr_{(t)}$ are computed from a previous session or from a series of biomarkers computed from a bio-signal obtained under a given condition.

19. The method for biofeedback training of a subject according to claim 10, further comprising:
    removing artefacts from the bio-signal of the subject before computing the time-series of biomarker values.

* * * * *